(12) United States Patent
Hernandez Altamirano et al.

(10) Patent No.: US 9,023,785 B2
(45) Date of Patent: *May 5, 2015

(54) GEMINI SURFACTANTS, PROCESS OF MANUFACTURE AND USE AS MULTIFUNCTIONAL CORROSION INHIBITORS

(71) Applicant: Instituto Mexicano del Petroleo, Mexico City (MX)

(72) Inventors: Raul Hernandez Altamirano, Mexico City (MX); Violeta Yasmin Mena Cervantes, Mexico City (MX); Luis Silvestre Zamudio Rivera, Mexico City (MX); Hiram Isaac Beltran Conde, Mexico City (MX); Simon Lopez Ramirez, Mexico City (MX)

(73) Assignee: Instituto Mexicano del Petroleo, Mexico City (MX)

( * ) Notice: Subject to any disclaimer, the term of this patent is extended or adjusted under 35 U.S.C. 154(b) by 61 days.

This patent is subject to a terminal disclaimer.

(21) Appl. No.: 13/945,307
(22) Filed: Jul. 18, 2013
(65) Prior Publication Data

US 2013/0340326 A1 Dec. 26, 2013

Related U.S. Application Data

(62) Division of application No. 12/967,520, filed on Dec. 14, 2010, now Pat. No. 8,518,868.

(30) Foreign Application Priority Data

Dec. 15, 2009 (MX) .................. MX/a/2009/013704

(51) Int. Cl.
| | |
|---|---|
| *C11D 1/62* | (2006.01) |
| *C10L 10/04* | (2006.01) |
| *C07C 229/12* | (2006.01) |
| *C09K 5/10* | (2006.01) |
| *C10G 75/02* | (2006.01) |

(Continued)

(52) U.S. Cl.
CPC .............. *C10L 10/04* (2013.01); *C07C 229/12* (2013.01); *C09K 5/10* (2013.01); *C10G 75/02* (2013.01);

(Continued)

(58) Field of Classification Search
CPC ........................................... C11D 1/62
USPC ........................................... 510/504
See application file for complete search history.

(56) References Cited

U.S. PATENT DOCUMENTS

| | | | |
|---|---|---|---|
| 3,390,085 A | 6/1968 | Floeck | |
| 3,623,979 A | 11/1971 | Maddox, Jr. et al. | |

(Continued)

FOREIGN PATENT DOCUMENTS

WO 00/30985 6/2000

OTHER PUBLICATIONS

Negm, N.A., et al., Corrosion Science 2010, vol. 52, issue 6, pp. 2122-2132, abstract only, no month available.

*Primary Examiner* — John Hardee
(74) *Attorney, Agent, or Firm* — Roylance, Abrams, Berdo & Goodman, L.L.P.

(57) ABSTRACT

Gemini surfactants of bis-N-alkyl polyether, bis-N-alkenyl polyether, bis-N-cycloalkyl polyether, bis-N-aryl polyether bis-beta or alpha-amino acids or their salts, are produced for use as multifunctional corrosion inhibitors, which protect and prevent corrosion of ferrous metals exposed to acidic, basic and neutral liquids when transporting or storing crude oil and liquid fuels. The surfactants are also used to inhibit corrosion of equipment and pipes used in cooling systems in petroleum and petrochemical equipment. The Gemini surfactants have the structural formula:

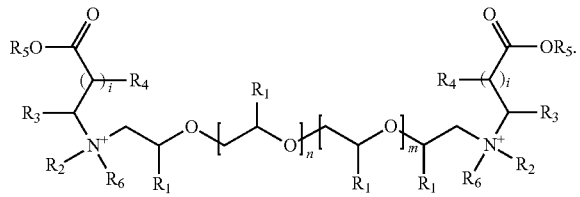

27 Claims, 1 Drawing Sheet

(51) Int. Cl.
   *C10L 1/14* (2006.01)
   *C10L 1/222* (2006.01)
   *C10L 1/223* (2006.01)
   *C10L 1/2387* (2006.01)
   *C23F 11/173* (2006.01)
   *C10L 1/12* (2006.01)
   *C10L 1/16* (2006.01)
   *C10L 1/182* (2006.01)

(52) U.S. Cl.
   CPC ............... *C10L 1/1208* (2013.01); *C10L 1/125* (2013.01); *C10L 1/14* (2013.01); *C10L 1/1608* (2013.01); *C10L 1/1616* (2013.01); *C10L 1/1824* (2013.01); *C10L 1/2222* (2013.01); *C10L 1/223* (2013.01); *C10L 1/2387* (2013.01); *C23F 11/173* (2013.01)

(56) References Cited

U.S. PATENT DOCUMENTS

| | | | |
|---|---|---|---|
| 3,629,104 A | 12/1971 | Maddox, Jr. | |
| 3,974,090 A | 8/1976 | Mitchell | |
| 4,003,842 A | 1/1977 | Suen et al. | |
| 4,214,876 A | 7/1980 | Garth et al. | |
| 4,234,511 A | 11/1980 | Buckman | |
| 4,388,214 A | 6/1983 | Oppenlaender et al. | |
| 4,509,951 A | 4/1985 | Knapp | |
| 4,511,366 A | 4/1985 | Burrows et al. | |
| 4,737,159 A | 4/1988 | Phillips | |
| 5,062,992 A | 11/1991 | McCullough | |
| 5,945,393 A | 8/1999 | Tracy et al. | |
| 5,952,290 A | 9/1999 | Li et al. | |
| 6,215,013 B1 | 4/2001 | Woodward et al. | |
| 6,572,789 B1 | 6/2003 | Yang et al. | |
| 8,518,868 B2 * | 8/2013 | Hernandez Altamirano et al. | 510/479 |
| 2003/0078176 A1 | 4/2003 | Elsner et al. | |
| 2003/0078182 A1 | 4/2003 | Kischkel et al. | |
| 2006/0024691 A1 | 2/2006 | Benz | |
| 2009/0054368 A1 | 2/2009 | Wettig et al. | |
| 2011/0269652 A1 | 11/2011 | Marangoni et al. | |

* cited by examiner

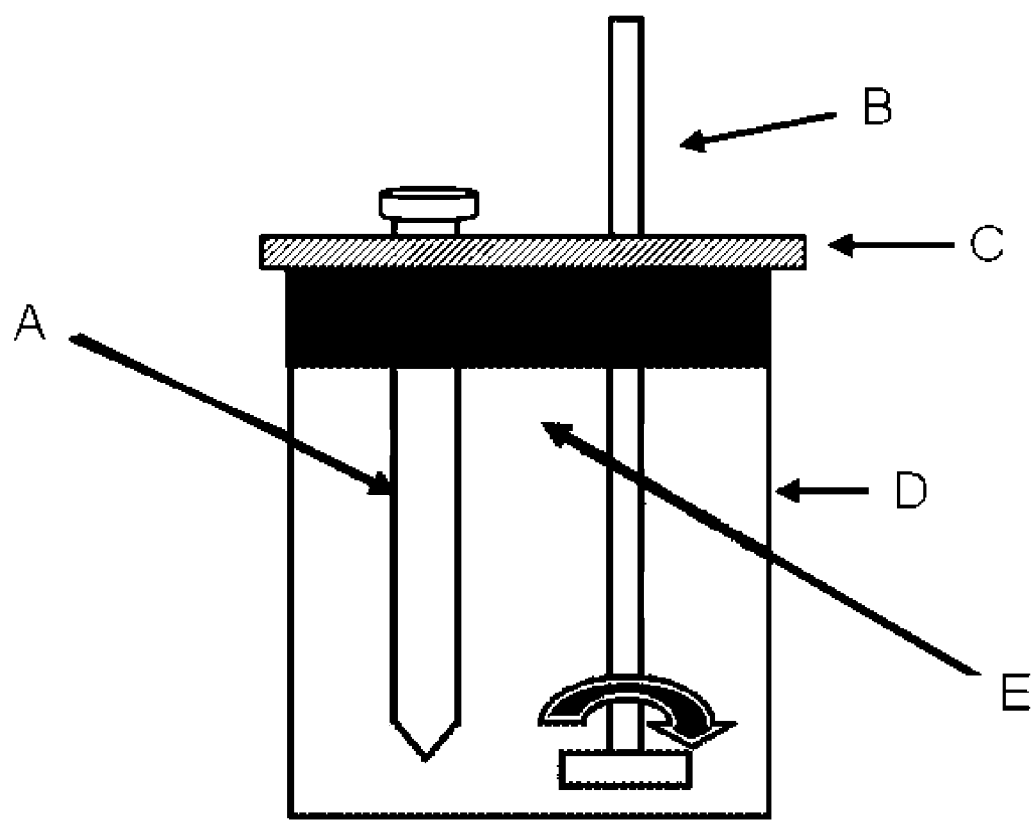

GEMINI SURFACTANTS, PROCESS OF MANUFACTURE AND USE AS MULTIFUNCTIONAL CORROSION INHIBITORS

CROSS-REFERENCE TO RELATED APPLICATION

This application is a divisional application of Ser. No. 12/967,520, filed Dec. 14, 2010, now U.S. Pat. No. 8,518,868, which application claims priority to Mexican Patent Application No. MX/a/2009/013704, filed Dec. 15, 2009, which is hereby incorporated by reference in its entirety.

FIELD OF THE INVENTION

The present invention is related with new gemini surfactants bis-N-alkylpolyether, bis-N-alkenylpolyether, bis-N-cycloalkylpolyether or bis-N-arylpolyether bis-beta or alpha amino acids or their salts, a process for producing the surfactants and use principally as multifunctional corrosion inhibitors, which protect and prevent of corrosion of:
  Ferrous metals that transported or stored crude oil and liquid fuels as primary fuel without desulfurizing, gasoline with low sulfur content, alkylated gasoline, jet fuel, diesel and MTBE, by the presence of acidic pollutants, sulfur compounds and water, exposed or not to oxygen, and
  Equipment and pipes used in cooling systems that use water characterized by a high concentration of divalent ions such as calcium and magnesium which are the main cause of producing pitting corrosion in this environment.

The gemini surfactants of the present invention and their formulations, have the characteristic of having a low environmental impact.

BACKGROUND OF THE INVENTION

In the oil industry throughout its supply chain there are several problems that cause daily losses of millions caused by falls in crude oil production, as well as failures caused by wear of pipelines and equipment, predominantly from corrosion problems, because of this is that globally the investigations are aimed at generating solutions through a variety of methods to minimize such problems.

Corrosion is a phenomenon that causes millions in losses in the oil industry, because it occurs in virtually all oil production chain from farm to processing it.

Corrosion is considered the progressive wear of a metallic material due to its interaction with the surrounding environment.

Corrosion taking place in environments characteristic of the petroleum industry can be caused by a large number of pollutants, among which hydrogen sulfide, carbon dioxide, organic acids, inorganic salts such as sodium chloride, ammonium cyanide, scales as barium sulfate, calcium carbonate, strontium sulfate and calcium sulfate and hydrochloric acid, among others, these pollutants cause loss of metallic material by uniform corrosion and pitting which can lead to serious accidents.

The corrosion phenomenon is also commonly found in transportation and storage of products derived from oil refining as gasoline without desulfurize, gasoline with low sulfur, diesel, alkylated gasoline, jet fuel, diesel and methyl tert butyl ether, from others.

The main damage caused by internal corrosion is uniform wear of the material, mainly due to the formation of iron sulfides and chlorides.

For the particular case of the services area, especially in cooling systems, the high concentration of divalent ions such as calcium and magnesium in the water used is the main factor of wear of piping and equipment, and accidents due to pitting corrosion. In this regard, it is important to note that both globally and in Mexico there is a tendency of increasing the production of heavy crude oils, which generally have a higher content of pollutants, as well as environmental regulations that increasingly restrict the use of water, the concentration of divalent ions such as calcium and magnesium is increased by evaporation of water lost to the environment, caused by heat exchange with other process fluids.

Because of this, the global trend in the area of chemicals is the development of corrosion inhibitors with a greater degree of versatility, capable of controlling the corrosion levels despite significant increases in contaminants in crude oil, fuel and water used in the process, which imparts a more aggressive characteristic.

Gemini surfactants are a family that is characterized by having in their molecules at least two hydrocarbon chains and two hydrophilic or polar groups:

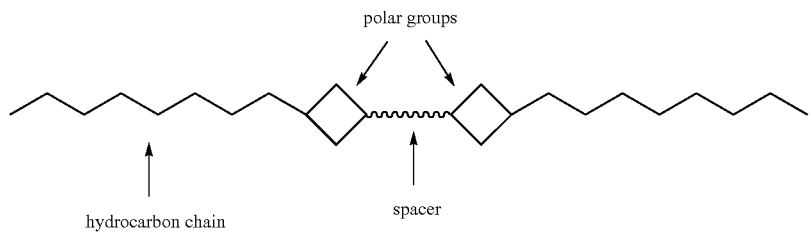 [SMILES: CCCCCCCCC1CC(C2CC(CCCCCCCC)C2)C1]

whereas the conventional surfactant molecules contain one or two hydrocarbon chains attached to the same polar group.

In this regard, most of the gemini surfactants in their molecules have a hydrocarbon chain, a polar group, a short hydrocarbon chain that acts as a bridge or spacer, a second polar group and a hydrocarbon chain.

The first synthesis of gemini surfactants was announced in 1971 by C. A. Bunton, L. Robinson, J. Schaak, M. F. Stam, University of California, who called them dication detergents. These researchers used gemini cationic surfactants as catalysts for certain reactions of nucleophilic substitution. The successive names taking these substances were bis-quaternary ammonium surfactants, dimeric surfactants, gemini surfactants and siamese surfactants.

In most of the gemini surfactants, the polar groups are ionic (cationic, anionic and, less frequently, amphoteric), but also synthesized surfactants with nonionic polar groups formed by polyethers. In the pioneering work of Bunton, Robinson, Schaak and Stam, the short hydrocarbon chain that acts as a bridge and linking the two parts of surfactant, each of which is consisting of a polar group, in this case a cation and a lipophilic chain.

Representative examples of new processes for obtaining gemini surfactants are:

U.S. Pat. No. 5,945,393 (A), issued Aug. 31, 1999, discloses obtaining gemini non-ionic surfactants based on alkyl phosphonates or sulfonates or alkyl aryl polyethers, and its application in the formulation of detergents and personal hygiene products.

U.S. Pat. No. 5,952,290 (A), issued Sep. 14, 1999, discloses obtaining base anionic gemini surfactants alkyl amides or alkyl aryl sulphonated and its application in the formulation of detergents and personal hygiene products.

U.S. Patent Publication No. 2003/078176 (A1), published Apr. 24, 2003, discloses obtaining surfactants with long chain alcohols and polyether derivatives of ethylene oxide and its application in detergent formulation.

U.S. Patent Publication No. 2003/078182 (A1), published Apr. 24, 2003, discloses obtaining base compositions of gemini surfactants 1,2-epoxy-alkane where the alkyl groups may be linear or branched, polyols derived from ethylene oxide and its application in detergents.

U.S. Patent Publication No. 2009/054368 (A1), published Feb. 26, 2009, discloses obtaining gemini surfactants quaternary amine base substituted alkyl or aryl groups such as pyrene and its application in the controlled release of active biological agents such as nucleic acids.

Representative examples of corrosion inhibitors used in acid environments of the oil industry are:

U.S. Pat. No. 3,623,979 (A), issued Nov. 30, 1971, relates to obtaining a base compound aminoalkyl-2-alkyl imidazolines and their use as corrosion inhibitors for ferrous metals in acidic characteristic of the oil industry. The efficiency of corrosion inhibition of these compounds was evaluated by gravimetric techniques.

U.S. Pat. No. 3,629,104 (A), issued Dec. 21, 1971, relates to the procurement of organic acid salts of compounds derived base 1-aminoalkyl-2-alkyl imidazolines and their use as corrosion inhibitors for ferrous metals in acidic characteristic of the oil industry. The efficiency of corrosion inhibition of these compounds was evaluated by gravimetric techniques U.S. Pat. No. 3,390,085 (A), issued Jun. 25, 1968, relates to a mixture containing an imidazoline salt prepared from the reaction of a fatty acid having 6 to 18 carbons with imidazoline selected from the group consisting of 1-aminoalkyl-2-alkyl-imidazoline and 1-hydroxyalkyl-2-alkyl imidazolines and their application as corrosion inhibitors in acidic characteristic of the oil industry.

U.S. Pat. No. 4,388,214 (A), issued Jun. 14, 1983, relates to corrosion inhibitors synthesized from the reaction of imidazoline salts and imidazolines with sulfur. These compounds are particularly useful for inhibiting corrosion of metal containers caused by carbon dioxide and hydrogen sulfide during transport and storage of crude oil.

U.S. Pat. No. 5,062,992 (A), issued Nov. 5, 1991, relates to a corrosion inhibiting formulation for oil and water systems, wherein the formulation is resistant to sludge formation and tends to stabilize oil in water. The corrosion inhibitor includes an imidazoline dissolved in an aromatic solvent, a 2-hydroxyalkyl carboxylic acid and glycol. The imidazoline is preferably prepared from the reaction of a long chain fatty acid and a polyamine.

Representative examples of corrosion inhibitors used in piping, tanks and other combustible handlers are:

U.S. Pat. No. 4,214,876 (A) (Corrosion inhibiting composition), issued Jul. 29, 1980, relates to the development of a formulation of the corrosion inhibition for ferrous metals exposed to hydrocarbon fuels comprising 75-95 weight percent of an unsaturated aliphatic carboxylic acid 16 to 18 carbons and 5 to 25 weight percent of succinic acid with a monoalkenyl chain in the range of 8 to 18 carbons, and use of a solvent hydrocarbon.

U.S. Pat. No. 4,509,951 (A) (Corrosion inhibitor for alcohol-based fuels and gasoline-alcohol mixtures), issued Apr. 9, 1985, relates to the development of a formulation of the corrosion inhibition for ferrous metals exposed to liquid fuels based in alcohol or gasoline-alcohol mixtures consisting of aliphatic carboxylic acid polyunsaturated with 18 carbons, and the reaction product of a polyamine with an alkenyl monounsaturated carboxylic acid or aliphatic or alkenyl succinic anhydride from 8 to 30 carbons.

U.S. Pat. No. 4,511,366 (A) (Liquid fuels and concentrates containing corrosion inhibitors), issued Apr. 16, 1985, relates to the development of a formulation of the corrosion inhibition for ferrous metals exposed to liquid alcohol-based fuel or gasoline-alcohol mixtures composed of an aliphatic carboxylic acid polyunsaturated 16 to 18 carbons and an alkenyl polyamine.

U.S. Pat. No. 4,737,159 (A) (Corrosion inhibitor for liquid fuels), issued Apr. 12, 1988, relates to the development of a formulation of the corrosion inhibition for ferrous metals exposed to liquid hydrocarbon fuels comprising 35-70 weight percent of monoalkenyl succinic acid with a chain from 8 to 18 carbons and 30 to 65 weight percent of an aliphatic or cycloaliphatic amine containing from 2 to 12 carbons and solvents, aromatic hydrocarbon compounds and alcohols of 1 to 4 carbons.

Representative examples of corrosion inhibitors used in cooling systems include:

U.S. Pat. No. 3,974,090 (A), issued Aug. 10, 1976, relates to obtaining alkali metal phosphonates and their application as corrosion inhibitors for cooling systems that use water with high content of divalent ions such as calcium and magnesium.

U.S. Pat. No. 4,003,842 (A), issued Jan. 18, 1977, relates to obtaining base compounds phosphonates, sulfonates and carboxylates derived from aliphatic alcohols and polyether derivatives of ethylene oxide and its application as corrosion inhibitors in cooling systems.

WO 00/30985 (A2), published on Jun. 2, 2000, relates to obtaining amino-phosphonates based compounds and use as corrosion and fouling inhibitors in cooling systems.

U.S. Pat. No. 4,234,511 (A), issued Nov. 18, 1980, relates to obtaining base compounds di-alkyl amino phosphonates and their application as corrosion inhibitors in aqueous systems and cooling towers.

U.S. Pat. No. 6,215,013 (B1), issued Apr. 10, 2001, relates to the obtaining of bisphosphonic acids and derivatives and their use as corrosion inhibitors in cooling systems present in the chemical industry.

U.S. Pat. No. 6,572,789 (B1), issued Jun. 3, 2003, relates to obtaining oligomers phosphine-succinic acid and their application as corrosion inhibitors in aqueous systems such as cooling towers.

SUMMARY OF THE INVENTION

The disadvantages of the prior compounds and processes are overcome by the present invention. The invention is directed to novel gemini surfactants bis-N-alkyl polyether, bis-N-alkenyl polyether, bis-N-cycloalkyl polyether, bis-N-aryl polyether bis-beta or alpha-amino acids or their salts, a production process for producing the surfactants, and the use of the surfactants as multifunctional corrosion inhibitors.

It is therefore an object of this invention to provide new gemini surfactants of bis-N-alkyl polyether, bis-N-alkenyl polyether, bis-N-cycloalkyl polyether, bis-N-aryl polyether bis-beta or alpha-amino acids or their salts.

An additional object of this invention is to provide the process for obtaining new gemini surfactants of bis-N-alkyl polyether, bis-N-alkenyl polyether, bis-N-cycloalkyl polyether, bis-N-aryl polyether bis-beta or alpha-amino acids or their salts.

Another object of this invention is to provide an alternative use of the new gemini surfactants bis-N-alkyl polyether, bis-N-alkenyl polyether, bis-N-cycloalkyl polyether, bis-N-aryl polyether bis-beta or alpha-amino acids or their salts as corrosion inhibitors of ferrous multifunctional found in contact with crude oil, hydrogen sulfide, carbon dioxide, cyanides, fuel liquids, brines saturated inorganic salts such as sodium chloride, calcium carbonate, calcium sulfate, strontium and barium sulfates and water with a high content of divalent ions such as calcium and magnesium, which is commonly used in cooling systems.

The features of the invention are attained by providing gemini surfactants bis-N-alkyl polyether, bis-N-alkenyl polyether, bis-N-cycloalkyl polyether, bis-N-aryl polyether bis-beta or alpha-amino acids or their salts having the formula:

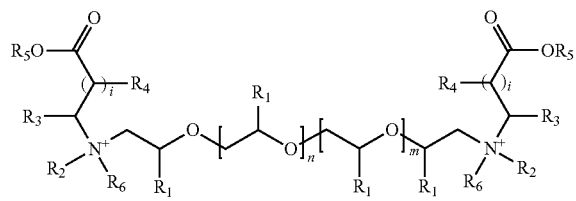

where:
- $R_1$ is a radical represented by —H or —$CH_3$,
- $R_2$ is an alkyl, alkenyl chain, cycloalkyl or aryl;
- $R_3$ is a radical represented by —H, —$CH_3$, —CH=CH—$CH_3$, or —COOX;
- $R_4$ is a radical represented by —H, —$CH_3$, or —$CH_2$—COOX;
- $R_5$ is a radical represented by —H, an alkyl, alkenyl, cycloalkyl, aryl group, or a metal;
- $R_6$ is a radical represented by an alkyl, alkenyl, cycloalkyl, or aryl group;
- n and m can have values from 1 to 250, depending on the molecular weight of polyether used, and
- i can have values of 0 and 1:
  - when i=1:
    - $R_3$ is a radical represented by —H, —$CH_3$, —CH=CH—$CH_3$, or —COOX, and
  - when i is equal to 0:
    - $R_3$ is a radical represented by —COOX.

In the radical —COOX used in $R_3$ and $R_4$, X is represented by:
- —H, an alkyl, alkenyl group, a cycloalkyl or aryl group, or a metal.

The invention is also directed to a method of inhibiting corrosion of ferrous metals in contact with a liquid selected from the group consisting of crude oil, liquid fuels and cooling water, said method comprising adding a corrosion inhibitor to said liquid, said corrosion inhibitor comprising gemini surfactants bis-N-alkyl polyether, bis-N-alkenyl polyether, bis-N-cycloalkyl polyether, bis-N-aryl polyether bis-beta or alpha-amino acids or their salts of the present invention as multifunctional corrosion inhibitors to protect and prevent corrosion of the ferrous metals exposed to acidic, basic and neutral environments where the surfactant is included at a concentration of 0.5 to 10,000 ppm based on the amount of the liquid.

BRIEF DESCRIPTION OF THE DRAWING

FIG. 1 shows the testing device used by the NACE TM-0172 method, to determine the efficiency of corrosion inhibition by new gemini surfactants of the present invention.

DETAILED DESCRIPTION OF THE INVENTION

The present invention is related with new gemini surfactants bis-N-alkyl polyether, bis-N-alkenyl polyether, bis-N-cycloalkyl polyether, bis-N-aryl polyether bis-beta or alpha-amino acids or their salts, a process for producing the surfactants and the use of the surfactants principally as multifunctional corrosion inhibitors, which protect and prevent of corrosion of:

- Ferrous metals that are used to transport or store crude oil and liquid fuels as primary fuel without desulfurizing, gasoline with low sulfur content, alkylated gasoline, jet fuel, diesel and MTBE, by the presence of acidic pollutants, sulfur compounds and water, exposed or not to oxygen, and
- Equipment and pipes used in cooling systems that use water characterized by a high content of divalent ions such as calcium and magnesium that are the main cause of producing pitting corrosion in this environment.

The gemini surfactants of the present invention and their formulations, have the characteristic of present low environmental impact.

The multifunctional corrosion inhibitors of the present invention relate to the new gemini surfactants bis-N-alkyl polyether, bis-N-alkenyl polyether, bis-N-cycloalkyl polyether, bis-N-aryl polyether bis-beta or alpha-amino acids or their salts, using distilled water as a solvent or brine with high content of divalent ions such as calcium, magnesium, strontium or barium, organic solvents or compounds derived from alcohols such as methanol, ethanol, isopropanol or mixtures thereof, or aromatics such as xylene, toluene, diesel, gasoline or mixtures thereof.

The new gemini surfactants bis-N-alkyl polyether, bis-N-alkenyl polyether, bis-N-cycloalkyl polyether, bis-N-aryl polyether bis-beta or alpha-amino acids or their salts of this invention have the structural formula:

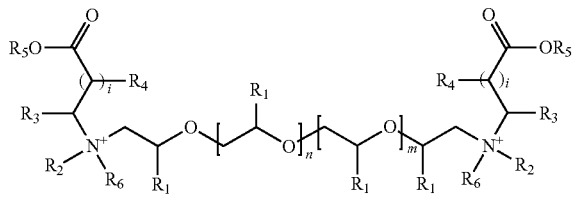

where:
- $R_1$ is a radical represented by —H or —$CH_3$,
- $R_2$ is a alkyl or alkenyl chain, linear or branched, preferably having 1 to 30 carbon atoms, or an cycloalkyl or aryl group, preferably having 5 to 12 carbon atoms;
- $R_3$ is a radical represented by —H, —$CH_3$, —CH=CH—$CH_3$, —COOX;
- $R_4$ is a radical represented by —H, —$CH_3$ or —$CH_2$, —COOX;
- $R_5$ is a radical represented by —H; an alkyl or alkenyl chain, that is linear or branched, preferably having 1 to 30 carbon atoms, a cycloalkyl or aryl group, preferably having 5 to 12 carbon atoms, or a metal, preferably being Na, K, Ca, Mg or Cs;
- $R_6$ is a radical represented by a linear or branched alkyl or alkenyl chain, preferably having 1 to 30 carbon atoms, or a cycloalkyl or aryl group preferably having 5 to 12 carbon atoms;
- n and m can have values from 1 to 250, depending on the molecular weight of polyether used, where the polyether used preferably is derived from ethylene oxide or propylene oxide or their copolymer whose molecular weight is in the range 100 to 20,000 g/mol; and
- i can have values of 0 and 1:
    when i=1:
      $R_3$ is a radical represented by —H, —$CH_3$, —CH=CH—$CH_3$, —COOX; and
    when i=0:
      $R_3$ is a radical represented by —COOX.

In the radical —COOX in $R_3$ and $R_4$, X are represented by:
—H; a linear or branched alkyl or alkenyl chain, preferably having 1 to 30 carbon atoms, a cycloalkyl or aryl group, preferably having 5 to 12 carbon atoms, or a metal, preferably being Na, K, Ca, Mg or Cs.

The invention is also directed to a method of inhibiting or preventing corrosion of metals and particularly ferrous metal using the gemini surfactants as a corrosion inhibitor by contacting the metal with the corrosion inhibitor. The corrosion inhibitor of the invention can include about 1 to 100 wt % of one or more of the gemini surfactants. The corrosion inhibitor containing the gemini surfactants can include a solvent such as water, distilled water, an aqueous brine solution or an organic solvent. The aqueous brine solution can contain a high concentration of divalent metal ions such as calcium, strontium, or barium. The organic solvent can be an alcohol such as methanol, ethanol, isopropanol or mixtures thereof. The organic solvent can also be an aromatic compound such as xylene, toluene, diesel fuel, gasoline or mixtures thereof.

The method of the invention can inhibit or prevent corrosion of equipment or prevent corrosion of equipment used for storing or transporting crude oil, liquid fuels and petroleum distillate such as pipelines and storage tanks. The method adds a corrosion inhibiting effective amount of the gemini surfactants of the invention to the crude oil, liquid fuel or petroleum distillates. Preferably, the gemini surfactants are included in an amount of about 0.5 ppm to about 10,000 ppm based on the amount of the crude oil, liquid fuel or petroleum distillate. The crude oil, liquid fuel or petroleum distillate containing the corrosion inhibitor is then passed through the equipment or pipeline.

The gemini surfactants are also suitable for use as corrosion inhibitors in cooling liquids and particularly aqueous cooling liquids for cooling machinery and various components used in the oil petrochemical and chemistical industries. In one embodiment of the invention, the method adds at least one of the gemini surfactants of the invention to an aqueous cooling fluid in an amount effective to inhibit or prevent corrosion of the machinery or components. Typically, the gemini surfactants are included in an amount of about 0.5 ppm to about 10,000 ppm.

The new gemini surfactants bis-N-alkyl polyether, bis-N-alkenyl polyether, bis-N-cycloalkyl polyether, bis-N-aryl polyether bis-beta or alpha-amino acids or their salts, of structural Formula XII, are prepared according to the following synthesis scheme:

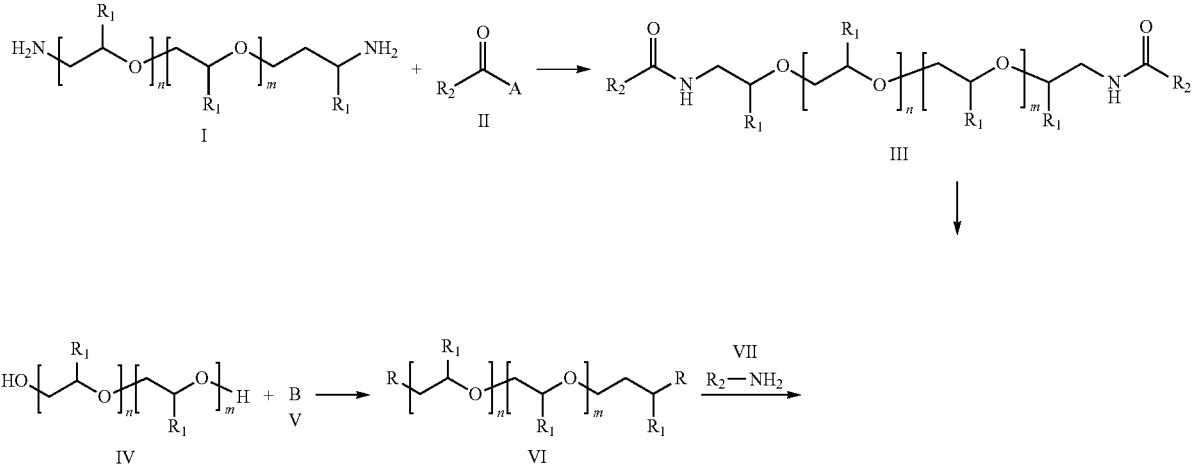

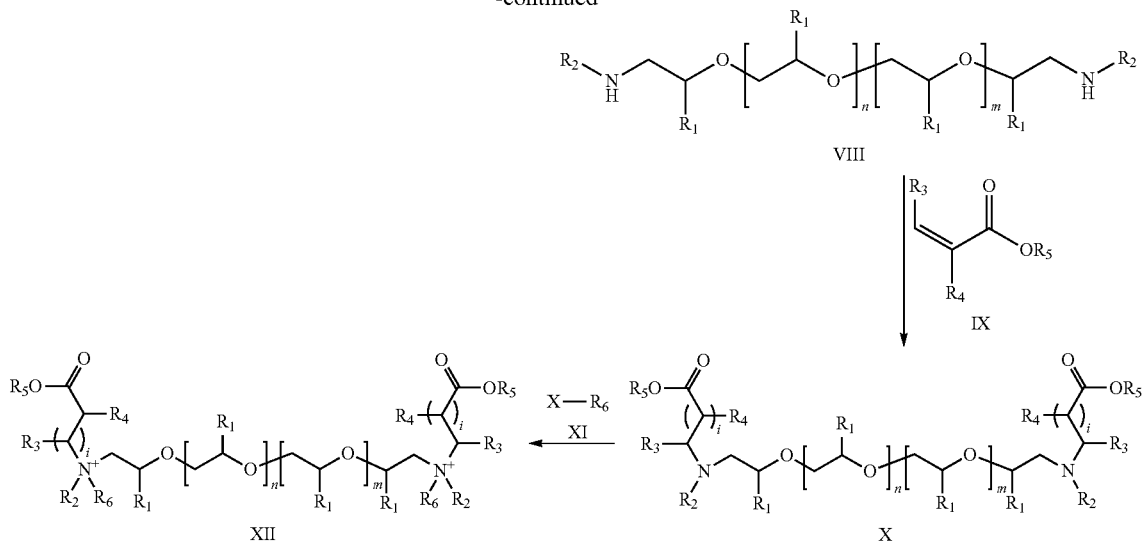

The reaction scheme of new gemini surfactants bis-N-alkyl polyether, bis-N-alkenyl polyether, bis-N-cycloalkyl polyether, bis-N-aryl polyether bis-beta or alpha-amino acids or their salts of structural formula XII, comprises three reaction steps:

I. The first stage of the reaction synthesis scheme is to obtain secondary amines of formula VIII bis-N-alkyl polyether, bis-N-alkenyl polyether, bis-N-cycloalkyl polyether, bis-N-aryl polyether, which can be done through two routes of synthesis:
  i. The first synthetic route is the formation of diamides of formula III, by reacting polyethers of formula I, preferably derived from ethylene oxide or propylene oxide or copolymers of these with two amino groups, one at the end and another at the beginning of the polymer chain whose molecular weight is in the range of 100 to 20,000 g/mol, with compounds of formula II, where A is derived from carboxylic acids, esters, halide alkyl or linear or branched alkenyl, preferably having 1 to 30 carbon atoms, or cycloalkyl or aryl, preferably having 5 to 12 carbon atoms; the diamides of formula III are reduced to their corresponding secondary amines of formula VIII using hydrides, preferably lithium aluminum hydride, or catalytic hydrogenation.
  ii. The second route of synthesis consists of two stages:
    The first step is to react polyalkyleneglycols of Formula IV, preferably derived from ethylene oxide and propylene oxide or copolymers of these having two hydroxyl groups, one at the end and the other at the beginning of the polymer chain whose molecular weight is in the range of 100 to 20,000 g/mol, with at least one of the compounds represented by the letter B: tosyl chloride, mesyl chloride, bromine or chlorine molecules, or penta or tri chloride or bromide phosphorous, preferably chloride tosyl, where the reaction is carried out with a molar ratio of polyglycols of Formula IV and B compounds of 1:2 to 1:4, preferably 1:2.2 to 1:2.6, with alkaline sodium potassium or cesium hydroxide, preferably sodium hydroxide, using water as a solvent, tetrahydrofuran or acetonitrile or mixtures thereof, a reaction time of 1 to 8 hours, preferably 3 to 5 hours at a temperature of 0 to 25° C., preferably from 5 to 20° C., to form compounds of Formula VI; and
    The second step consists of reacting the compounds of Formula VI via nucleophilic substitution with compounds of Formula VII: linear or branched alkyl or alkenyl amines, preferably having 1 to 30 carbon atoms, or cycloalkyl or aryl, preferably having 5 to 12 carbon atoms, wherein the reaction is carried out with a molar ratio between the compounds of Formula VI and VII of 1:1.5 to 1:4, preferably 1:1.8 to 1:2.6, in the presence of solvents such as acetonitrile, dimethylformamide, dimethylsulfoxide, acetone or short chain alcohols, preferably acetonitrile, at a reaction time of 1 to 10 hours, preferably 4 to 6 hours, and at a temperature of 60 to 100° C., preferably 70 to 85° C.; to obtain secondary amines of Formula VIII.

II. The second stage of reaction synthesis scheme is to obtain compounds of Formula X: bis-N-alkyl polyether, bis-N-alkenyl polyether, bis-N-cycloalkyl polyether, bis-N-aryl polyether bis-beta or alpha-amino acids or their salts, which are obtained by reacting secondary amines of Formula VIII with compounds of Formula IX: unsaturated acids such as acrylic, methacrylic, itaconic, crotonic, fumaric, isocrotonic, angelic and maleic acids, among others, alpha or beta acids or halogenated as chloro-acetic acid, acetic bromine, bromine and chlorine propionic, or salts of the above acids, or unsaturated esters such as methyl acrylate and methyl methacrylate, among others, in which the reaction is carried out with respect molar among the compounds of Formula VIII and IX of 1:1.5 to 1:4, preferably 1:1.8 to 1:2.6. The reaction can be carried out in the absence or presence of solvents such as water, alcohols, aromatic hydrocarbon solvents or inert solvents, preferably water, toluene or xylene mixtures, o-xylene, m-xylene, p-xylene, kerosene and jet fuel. The reaction time, temperature and pressure depend on the structure of the compounds of Formula VIII and IX. Usually the reaction time varies from 1 to 24 hours, preferably 1 to 10 hours. The temperature ranges from 40 to 180° C., preferably 80 to 130° C., and the pressure is generally atmospheric, and can vary from 585 to 760 mmHg. The compounds of Formula X can be neutralized with bases such as hydroxides, carbonates or bicarbonates of sodium, potassium or cesium.

III. Finally, the third stage of reaction synthesis scheme is to obtain compounds of structural Formula XII, which corresponds to the new gemini surfactants bis-N-alkyl polyether, bis-N-alkenyl polyether, bis-N-cycloalkyl polyether, bis-N-aryl polyether bis-beta or alpha-amino acids or their salts which are obtained by reacting compounds of Formula X with compounds of Formula XI: halides such as bromide, chloride or iodide linear or branched alkyl or alkenyl, preferably having 1 to 30 carbon atoms, or cycloalkyl or aryl, preferably having 5 to 12 carbon atoms, with a molar ratio between the compounds of Formula X and XI of 1:1 to 1:4, preferably 1:1.5 to 1:2.6. The reaction can be carried out in the absence or presence of solvents such as water, alcohols, aromatic hydrocarbon solvents or inert solvents, preferably water, toluene or xylene mixtures, o-xylene, m-xylene, p-xylene, kerosene and jet fuel. The reaction time, temperature and pressure depend on the structure of the structures of the compounds of Formula X and XI. The reaction time usually ranges from 1 to 24 hours, preferably 1 to 10 hours. The temperature ranges from 15 to 90° C., preferably 25 to 50° C. and usually at atmospheric pressure, and can vary from 585 to 760 mmHg.

Some practical examples for better understanding of the present invention, without limiting its scope, are discussed below.

EXAMPLE 1

Preparation of 4,43-di(octadec-9-enyl)-7,10,13,16, 19,22,25,28,31,34,37,40-dodecaoxa-4,43-diaza-hexatetracontane-1,46-dioic acid. (Product 1)

In a 500 ml round bottom balloon flask containing 59 g of an aqueous solution to 17 weight percent of sodium hydroxide (10 g) were added 50 g of polyethylene glycol whose number average molecular weight is 600 g/mol, the mixture stirred for 20 minutes. Then, at room temperature (25° C.) and atmospheric pressure (585 mmHg), very slowly 87 g of a solution of tosyl chloride at 40 weight percent (34.8 g) in tetrahydrofuran were added, keeping the temperature below 25° C. throughout the addition. After completion of addition, the reaction mixture was stirred for about an hour at room temperature and atmospheric pressure. Then the reaction mixture was made and extraction of organic phase and evaporated the solvent at reduced pressure, to obtain 74 g of Product A as a viscous clear yellow liquid with a yield of 98%.

As a second stage of reaction in a 500 ml balloon flask, equipped with a magnetic stirrer and a condenser were added 111 g of acetonitrile, 74 g of Product A, 43 g of oleylamine and 34 g of potassium carbonate. The reaction mixture was stirred vigorously at reflux temperature and atmospheric pressure for five hours, after which time the reaction mixture was filtered and the solution was evaporated to remove the solvent under reduced pressure. Finally the crude reaction product was evaporated to remove the solvent under reduced pressure. The crude reaction product was subjected to a solvent extraction and the organic phase was evaporated under reduced pressure, yielding 81 g of Product B as a clear liquid viscous yellow with a yield of 92%.

For the third reaction stage in a three-necked round bottom flask of 250 ml, equipped with a magnetic stirrer, a dropping funnel, a thermometer and a condenser were added 81 g of Product B at room temperature and atmospheric pressure and 10.6 g of acrylic acid were slowly added. The reaction mixture was stirred vigorously at a temperature not exceeding 100° C. and atmospheric pressure for 3 hours. It is noteworthy that the reaction is exothermic and it is important to keep the reaction below 100° C. When the reaction time was completed 89 g of the Product 1 were obtained as a very viscous clear yellow liquid, with a yield of 95%. The product may or may not be neutralized with an alkaline base such as potassium or sodium hydroxide, or tertiary amine quaternized using alkyl or alkenyl or aryl halides such as propyl or benzyl bromide or chloride.

The spectroscopic characteristics output 1 are:
Representative bands of FTIR ($cm^{-1}$, film): 3449, 3005, 2922, 2853, 1729, 1585, 1463, 1349, 1323, 1297, 1246, 1106, 1032, 845.
Representative chemical shifts of NMR $^1$H ($CDCl_3$), 200 MHz, δ (ppm): 5.27, 3.57, 3.09, 2.99, 2.86, 2.54, 2.47, 1.95, 1.19, 0.81.
Representative chemical shifts of NMR $^{13}$C ($CDCl_3$), 50 MHz, δ (ppm): 174.7, 129.8, 129.5, 72.6, 70.3, 53.1, 51.7, 50.2, 50.0, 32.4, 31.7, 29.6, 29.5, 29.3, 27.0, 22.5 and 13.9.

EXAMPLE 2

Preparation of 4,31-di(octadec-9-enyl)-7,10,13,16, 19,22,25,28-octaoxa-4,31-diazatetratriacontane-1, 34-dioic acid. (Product 2)

The Product 2 was obtained under the same scheme of synthesis of Product 1. For this product is used a polyethylene glycol with an average molecular weight of 400 g/mol.

The spectroscopic characteristics of Product 2 are:
Representative bands of FTIR ($cm^{-1}$, film): 3445, 3003, 2922, 2853, 1722, 1586, 1464, 1350, 1295, 1248, 1105, 947, 847.
Representative chemical shifts of NMR $^1$H ($CDCl_3$), 200 MHz, δ (ppm): 5.26, 3.56, 3.01, 2.98, 2.78, 2.50, 2.47, 1.94, 1.18, 0.80.
Representative chemical shifts of NMR $^{13}$C ($CDCl_3$), 50 MHz, δ (ppm): 175.1, 129.8, 129.5, 72.6, 70.3, 53.0, 51.7, 50.3, 50.0, 32.4, 31.7, 29.5, 29.3, 29.1, 27.0, 22.5 y 13.9.

EXAMPLE 3

Preparation of 4,16-di(octadec-9-enyl)-7,10,13-trioxa-4,16-diazanonadecane-1,19-dioic acid. (Product 3)

The Product 3 was obtained under the same scheme of synthesis of Product 1. For this product is used a polyethylene glycol with an average molecular weight of 200 g/mol.

The spectroscopic characteristics of Product 3 are:
Representative bands of FTIR ($cm^{-1}$, film): 3442, 3004, 2922, 2852, 1718, 1575, 1464, 1351, 1291, 1217, 1119, 965, 833.
Representative chemical shifts of NMR $^1$H ($CDCl_3$), 200 MHz, δ (ppm): 5.30, 3.60, 3.14, 2.99, 2.85, 2.55, 2.51, 1.96, 1.23, 0.84.
Representative chemical shifts of NMR $^{13}$C ($CDCl_3$), 50 MHz, δ (ppm): 175.0, 129.9, 129.6, 70.6, 53.2, 51.8, 50.2, 50.0, 32.5, 31.8, 29.6, 29.4, 29.2, 27.1, 22.6 and 14.0.

EXAMPLE 4

Preparation of 4,43-didodecyl-7,10,13,16,19,22,25, 28,31,34,37,40-dodecaoxa-4,43-diazahexatetracontane-1,46-dioic acid. (Product 4)

The Product 4 was obtained under the same scheme of synthesis of Product 1. For this product is used a polyethylene glycol with an average molecular weight of 600 g/mol and dodecylamine.

The spectroscopic characteristics of Product 4 are:
Representative bands of FTIR (cm$^{-1}$, film): 3446, 2921, 2854, 1723, 1572, 1461, 1348, 1291, 1211, 1115, 962, 830.
Representative chemical shifts of NMR $^1$H (CDCl$_3$), 200 MHz, δ (ppm): 3.58, 3.12, 3.03, 2.93, 2.56, 2.47, 1.19, 0.82.
Representative chemical shifts of NMR $^{13}$C (CDCl$_3$), 50 MHz, δ (ppm): 174.6, 72.4, 70.5, 53.0, 51.6, 50.1, 50.0, 31.7, 29.4, 29.3, 29.1, 26.8, 22.5 and 14.0.

EXAMPLE 5

Preparation of 4,31-didodecyl-7,10,13,16,19,22,25, 28-octaoxa-4,31-diazatetratriacontane-1,34-dioic acid. (Product 5)

The Product 5 was obtained under the same scheme of synthesis of Product 1. For this product is used a polyethylene glycol with an average molecular weight of 400 g/mol and dodecylamine.

The spectroscopic characteristics of Product 5 are:
Representative bands of FTIR (cm$^{-1}$, film): 3451, 2929, 2851, 1715, 1568, 1462, 1359, 1289, 1114, 961, 832.
Representative chemical shifts of NMR $^1$H (CDCl$_3$), 200 MHz, δ (ppm): 3.58, 3.12, 3.03, 2.93, 2.56, 2.47, 1.19, 0.82.
Representative chemical shifts of NMR $^{13}$C (CDCl$_3$), 50 MHz, δ (ppm): 174.6, 72.4, 70.5, 53.0, 51.6, 50.1, 50.0, 31.7, 29.4, 29.3, 29.1, 26.8, 22.5 and 14.0.

EXAMPLE 6

Preparation of 4,16-didodecyl-7,10,13-trioxa-4,16-diazanonadecane-1,19-dioic acid. (Product 6)

The Product 6 was obtained under the same scheme of synthesis of Product 1. For this product is used a polyethylene glycol with an average molecular weight of 200 g/mol and dodecylamine.

The spectroscopic characteristics of Product 6 are:
Representative bands of FTIR (cm$^{-1}$, film): 3449, 2924, 2856, 1721, 1567, 1456, 1355, 1295, 1214, 1125, 954, 829.
Representative chemical shifts of NMR $^1$H (CDCl$_3$), 200 MHz, δ (ppm): 3.50, 3.10, 3.05, 2.84, 2.47, 2.45, 1.14, 0.76.
Representative chemical shifts of NMR $^{13}$C (CDCl$_3$), 50 MHz, δ (ppm): 174.7, 70.2, 54.3, 54.0, 53.0, 52.3, 31.6, 29.3, 29.2, 29.0, 22.4 and 13.8.

Performance Testing of the Gemini Surfactants as Corrosion Inhibitors in Various Corrosive Environments To evaluate the efficiency of corrosion inhibition in acidic environments, basic and neutral characteristic of the petroleum, petrochemical and chemical industries, were used gravimetric and electrochemical techniques and methods set out in NACE technical documents 1D NACE-182 and NACE TM-172.

The following describes each test procedures and results. Determination of the Corrosion Inhibition Efficiency Through NACE 1D-182 Method.

For this test using a specimen of 1010 carbon steel with dimensions 2,540×1,270 cm×0.025 cm, which is weighed and placed inside a bottle containing 180 ml of an emulsion or brine aggressive environments simulating acids characteristic of the oil industry, and a certain amount of corrosion inhibitor which can vary from 0 to 500 ppm. The bottle is sealed and placed in a hole of a wheel having a diameter of 58.4 cm that is within a range, and then the oven temperature is increased to 70° C., while the wheel rotates at 30 rpm for about 46 hours. At the end of the test, the specimen is removed from the bottle, washed consecutively with chloroform, acetone, water, a solution of diluted hydrochloric acid, a potassium bicarbonate solution with 5 in weight and water, cleaned with wire brushing, rinsed with soap and water, dried in an oven at 60° C. and reweighed. Depending on weight loss and with reference to a target is calculated efficiency of corrosion inhibition, while for the evaluation of the corrosion rate reported in thousandths of an inch per year (mpy) are taken into account the following parameters the specimen: a) weight loss, b) area, c) density d) test time.

Gravimetric test commonly called dynamic wheel (Wheel test) is a dynamic procedure developed for fluids (oil, water and inhibitor) that simulates the corrosive environment characteristic of oil production.

Testing Equipment and Reagents:
a) Evaluating dynamic for corrosion inhibitors with temperature controller, stirrer speed of 30 rpm and capacity for 52 bottles of 180 ml.
b) Bottles of 200 ml of capacity.
c) Coupon SAE 1010 carbon steel, 2,540×1,270×0.025 cm (1"×0.5"×0.010").
d) Glassware for the preparation of a corrosive environment. This consist of a glass reactor of 2 liter, equipped with a cooling bath, mechanical stirrer, bubbler for gas (nitrogen and hydrogen sulfide), has an outlet connected to two traps in series (the first with sodium hydroxide in pellet form and the second with another sodium hydroxide solution 20% in weight), so that hydrogen sulfide does not contaminate the environment.
e) Potentiometer for measuring pH.

The test conditions are shown in Table 1, while the composition of the brine used is shown in Table 2.

TABLE 1

Test Conditions, NACE 1D-182 method.

| | |
|---|---|
| Temperature | 70° C. |
| Aqueous medium | Synthetic brine with 600 ± 50 ppm de H$_2$S |
| Test time | 46 hours |
| Organic medium | Kerosene |
| Volume ratio | 90/10 |
| Synthetic brine/organic medium | |
| Test volume | 180 ml |
| pH | 4 |
| Metals coupons | Steel SAE 1010 |

TABLE 2

Brine composition used, 1D-182 NACE method.

| Salts | Amount (g/l) |
|---|---|
| NaCl | 60.0 |
| CaCl$_2$•H$_2$O | 6.0 |
| MgCl$_2$•6H$_2$O | 10.48 |
| Na$_2$SO$_4$ | 3.5 |

Results:
The difference in weight of the coupons before and after being exposed to corrosive liquid for 46 hours is a direct indication of metal lost due to corrosion.

The efficiency of corrosion inhibition is obtained by comparing the reference coupon wear with the wear of the coupons with corrosion inhibitor at different concentrations, using the following formula:

$$\% E = (Vo - V)/V \times 100$$

where:
 Vo=Corrosion velocity of reference coupon.
 V=Corrosion velocity of coupon with corrosion inhibitor.

Table 3 shows the results of corrosion rate and efficiency on Products 1 to 6 of the present invention, used at different concentrations.

TABLE 3

Corrosion rate and efficiency of Products 1 to 6, at different concentrations.

| Product | Concentration, (ppm) | Corrosion velocity, (mpy's)* | Efficiency, (%) |
|---|---|---|---|
| Reference | 0 | 41.6 | 0 |
| 1 | 10 | 2.2 | 94.9 |
| 1 | 25 | 3.5 | 91.9 |
| 1 | 50 | 2.4 | 94.5 |
| 1 | 75 | 2..0 | 95.2 |
| 2 | 10 | 5.8 | 86.4 |
| 2 | 25 | 4.2 | 90.1 |
| 2 | 50 | 2.8 | 91.4 |
| 2 | 75 | 0.6 | 98.5 |
| 3 | 10 | 4.6 | 89.3 |
| 3 | 25 | 1.4 | 96.7 |
| 3 | 50 | 1.4 | 96.7 |
| 3 | 75 | 1.6 | 95.9 |
| 4 | 10 | 32.4 | 24.3 |
| 4 | 25 | 26.4 | 38.2 |
| 4 | 50 | 5.2 | 87.9 |
| 4 | 75 | 2.9 | 93.0 |
| 5 | 10 | 19.6 | 54.0 |
| 5 | 25 | 5.7 | 86.8 |
| 5 | 50 | 3.3 | 92.3 |
| 5 | 75 | 2.2 | 94.9 |
| 6 | 10 | 3.1 | 92.5 |
| 6 | 25 | 2.9 | 92.8 |
| 6 | 50 | 3.1 | 92.5 |
| 6 | 75 | 2.8 | 93.2 |

*mpy's: thousandths of an inch per year.

The results presented in Table 3 shows that the efficiency of new gemini surfactants of this invention is above 90% at concentrations above 50 ppm. At low concentration (10 ppm), the efficiency depends on size of the hydrophobic chains and the size of polyether employed (molecular weight) suggesting that long-chain hydrophobic promotes the repulsion of water molecules to the metal surface through a steric effect. Determination of the Efficiency of Corrosion Inhibition by the Method NACE TM-0172.

Test Description:
 Test Method NACE TM-0172 is to determine the corrosive properties of gasoline, jet fuel and distillate fuels that found in pipelines and storage tanks. Also includes information on metal specimen preparations, equipment and a system for ranking the test samples with corrosion inhibitor.

Testing Equipment and Apparatus:
 The apparatus consists of:
 A temperature measuring device, and
 One bath vessel. Should be used a thermally controlled bath of mineral oil capable of maintaining a temperature in the test sample 38±1° C. The bath vessel must have a cover with holes to accommodate the test glass and the temperature measuring device.

The test device used by the NACE TM-0172 method to determine the efficiency of corrosion inhibition posed by gemini surfactants of the present invention, illustrated by FIG. 1, consists of a test specimen (A), a digitally controlled stirrer (B), a cover of poly (tetrafluoroethylene) (C), a glass (D) and hydrocarbon-water mixture (E).

The sample must be a steel yarn 81.0×12.7 mm, the steel shall conform to UNS* G10150 (Grade 1015), UNS G10180 (1018), UNS G10200 (1020) or UNS G10250 (1025) ASTM A108, used with a plastic handle of poly(tetrafluoroethylene) (PTFE). (* Unified Numbering System).

Test Procedure:
 Add 300 ml of fuel to the test vessel and dispensed corrosion inhibitor to the desired concentration. The glass is placed in an oil bath at a temperature of 38±1° C. After 30 minutes of continuous stirring add 30 ml of distilled water, and continuous agitation for three hours. Subsequently the sample is removed, and left to drain and washed with toluene or xylene followed by acetone.

Sample Qualification: The rating should be based solely on the portion of the sample that remained in the test fluid. The corrosion products formed during the test have had limited opportunity to darken, and all deposits of solids not removed by washing of toluene and acetone should be considered as products of corrosion. Marks on the circle can occur during polishing and should not be interpreted as corrosion; classification is based according to Table 4.

TABLE 4

Samples qualification, NACE TM-0172 method.

| Qualification | Percent of corroded surface |
|---|---|
| A | 0 |
| B++ | Less than 0.1 (2 or 3 spots of no more than 1 mm in diameter). |
| B+ | Less than 5 |
| B | 5 a 25 |
| C | 25 a 50 |
| D | 50 a 75 |
| E | 75 a 100 |

Table 5 shows the results of the corrosion inhibition efficiency of product 1 with a variety of liquid fuels, according to NACE TM-0172 method.

TABLE NO. 5

Product 1 qualification, when used with a variety of liquid fuels. NACE TM-0172 method.

| Product | Concentration, (ppm) | Test medium, (fuel) | Qualification, (NACE TM-0172) |
|---|---|---|---|
| Reference | 0 | All fuels | E |
| 1 | 10 | Primary gasoline (without desulfurize) | B++ |
| 1 | 10 | Magna gasoline | A |
| 1 | 10 | Premium gasoline | A |
| 1 | 10 | Diesel | B++ |
| 1 | 10 | MTBE | A |
| 1 | 10 | Alkylated gasoline | A |
| 1 | 10 | Magna gasoline/ Ethanol (50:50) | A |

From the results shown in Table 5 the new Gemini surfactant (Product 1) at low concentration (10 ppm) passes the test with B++ and A, when used a variety of liquid fuels.

Table 6 shows the results of the efficiency of corrosion inhibition by the Products 2 to 6 of the present invention, when used gasoline with low sulfur content at different concentrations, according to NACE TM-0172 method.

TABLE 6

Qualifications of Products 2 to 6 of the present invention, when used gasoline with low sulfur content at different concentrations, NACE TM-0172 method.

| Product | Concentration, (ppm) | Qualification, (NACE TM-0172) |
|---------|----------------------|-------------------------------|
| Reference | 0 | E |
| 2 | 10 | B+ |
| 2 | 25 | B++ |
| 3 | 10 | B+ |
| 3 | 25 | A |
| 4 | 10 | B++ |
| 4 | 25 | B++ |
| 5 | 10 | B+ |
| 5 | 25 | B++ |
| 6 | 10 | B++ |
| 6 | 25 | A |

From the results shown in Table 6 that the new gemini surfactants of the present invention, at a concentration of 25 ppm pass the test of corrosion inhibition with a grade B++ and A. At low concentration (10 ppm) only the Products 4 and 6 pass the test.

From the above it is concluded that the efficiency of corrosion inhibition depends on the size of the hydrophobic chains and, for the particular test, the balance between the size of the spacer or bridge used and the length of the hydrocarbon chains.

Determination of the Efficiency of Corrosion Inhibition by Electrochemical Techniques.

Equipment Used:

A glass electrochemical cell, reference electrode, working electrode, counter electrode, pH meter, multimeter, potentiostat/galvanostat Autolab PGSTAT 30 71410 were used. A bitter brine of pH 4 was prepared and the dissolution of chemicals in isopropanol in order to prepare dissolution of 1,000 ppm in 100 ml.

Test Procedure:

A specimen of carbon steel 1010 with area of 0.5 cm² by grinding with 600 grit sandpaper. The bitter brine is the same as was used for the gravimetric technique. Polarization curves were generated linear open-circuit potential ±25 mV. The polarization curve is obtained and analyzed to determine the corresponding corrosion rate. To make a new experiment is necessary to perform the roughing electrode is placed in the cell and generate another curve. This procedure is repeated until there is a coincidence of at least two curves. The experiments were performed at room temperature with magnetic stirring and bitter brine adjusted to pH 4.0±1. The corrosion rate (mpy) is determined through manipulation of the curve using the program of the potentiostat.

Table 7 shows the results of the corrosion inhibition efficiency by the Products 1 to 4 of the present invention, at different concentrations, using electrochemical techniques:

TABLE 7

Efficiency of corrosion inhibition of Products 1 to 4, of the present invention, at different concentrations, using electrochemical techniques

| Product | Concentration, (ppm) | Corrosion velocity, (mpy's) | Efficiency, (%) |
|---------|----------------------|------------------------------|------------------|
| Reference | 0 | 72 | 0 |
| 1 | 25 | 18 | 75 |
| 1 | 50 | 12 | 83 |
| 2 | 25 | 21 | 71 |
| 2 | 50 | 18 | 75 |
| 3 | 25 | 16 | 78 |
| 3 | 50 | 12 | 83 |
| 4 | 25 | 16 | 78 |
| 4 | 50 | 12 | 83 |

From the results shown in Table 7 show that the corrosion inhibition efficiencies are maintained above 70% at concentrations of 25 and 50 ppm, and these concentrations are sufficient to protect the metal surface of the aggressive environment.

Determination of the Corrosion Inhibition Efficiency in Water of Cooling Systems Present in the Petroleum, Petrochemical and Chemical Industries.

A specimen of 1010 carbon steel with dimensions 2,540×1,270 cm×0.025 cm, which is weighed and placed inside a bottle containing 180 ml of hard water (high concentration of divalent ions of calcium and magnesium) that simulates the environment of cooling systems present in the petroleum, petrochemical and chemical industries, and a certain amount of corrosion inhibitor which can vary from 0 to 500 ppm. The bottle is sealed and placed in a hole of a wheel having a diameter of 58.4 cm that is inside an oven. Then the oven temperature is increased to 40° C., while the wheel rotates at 30 rpm for about 16 hours. At the end of the test, the specimen is removed from the bottle, washed consecutively with chloroform, acetone, water, a solution of diluted hydrochloric acid, a potassium bicarbonate solution to 5 weight percent and water, cleaned with wire brushing, rinsed with soap and water, dried in an oven at 60° C. and reweighed. Depending on weight loss and with reference to a target is calculated efficiency of corrosion inhibition, while for the evaluation of the corrosion rate reported in thousandths of an inch per year (mpy) are taken into account the following parameters the specimen: a) weight loss, b) area, c) density d) test time.

Gravimetric test is commonly called dynamic wheel (Wheel test) that simulates the corrosive environment typical of environments found in cooling systems.

The test conditions are shown in Table 8, while the composition of the brine is shown in Table 9.

TABLE 8

Test Conditions, Corrosion inhibition in water of cooling systems present in the petroleum, petrochemical and chemical industries.

| | |
|---|---|
| Temperature | 60° C. |
| Aqueous medium | Synthetic hard water |
| Test time | 16 hours |
| Test volume | 180 ml |
| Medium pH | 8.4 |
| Coupon sample | Carbon steel SAE 1010 |

TABLE 9

Brine composition, Corrosion inhibition in water of cooling systems present in the petroleum, petrochemical and chemical industries.

| Salts | Amount, (mg/l) |
|---|---|
| $CaCl_2$ | 360 |
| $MgSO_4$ | 200 |
| $NaHCO_3$ | 100 |

Results:

The difference in weight of the coupons before and after being exposed to corrosive liquid for 16 hours, and the presence of pitting, is a direct indication of metal lost due to corrosion.

Table 10 shows the efficiency results that showed the Products 1 and 2 of this invention, used at different concentrations.

TABLE 10

Efficiency of Products 1 and 2 of the present invention, at different concentrations

| Product | Concentration, (ppm) | Efficiency, (%) |
|---|---|---|
| Reference | 0 | 0 |
| 1 | 10 | 51.4 |
| 1 | 25 | 73.4 |
| 1 | 50 | 87.3 |
| 1 | 75 | 93.1 |
| 2 | 10 | 26.8 |
| 2 | 25 | 49.5 |
| 2 | 50 | 78.4 |
| 2 | 75 | 93.1 |

Note:
None of the coupons showed pitting

From the results shown in Table 10 the Products 1 and 2 have the ability to inhibit pitting or localized corrosion, providing better results at a concentration of 75 ppm, due to its solubility in water, mainly through two mechanisms: 1) Formation of film on the metal surface and 2) Formation of coordination complexes with ions in solution to avoid precipitation.

What is claimed is:

1. A process for producing bis-N-alkyl polyether, bis-N-alkenyl polyether, bis-N-cycloalkyl polyether, bis-N-aryl polyether bis-beta or alpha-amino acids or their salts having the formula XII

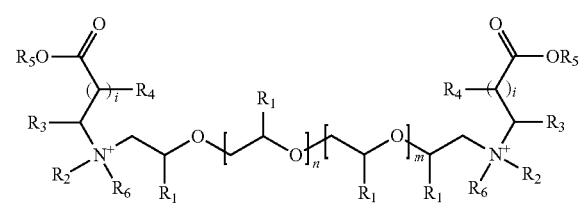

where:
$R_1$ is independently a radical represented by —H or —$CH_3$;
$R_2$ is an alkyl, alkenyl chain, cycloalkyl or aryl;
$R_3$ is a radical represented by —H, —$CH_3$, —CH=CH—$CH_3$, or —COOX;
$R_4$ is a radical represented by —H, —$CH_3$, or —$CH_2$—COOX;

$R_5$ is a radical represented by —H, an alkyl, alkenyl, cycloalkyl, aryl group, or a metal;
$R_6$ is a radical represented by an alkyl, alkenyl, cycloalkyl, or aryl group;
n and m can have values from 1 to 250, and
i can have values of 0 and 1:
  when i=1:
    $R_3$ is a radical represented by —H, —$CH_3$, —CH=CH—$CH_3$, or —COOX, and
  when i is equal to 0:
    $R_3$ is a radical represented by —COOX;
In the radical —COOX used in $R_3$ and $R_4$, X is represented by:
—H, an alkyl, alkenyl group, a cycloalkyl or aryl group, or a metal;
wherein said process comprises the reaction scheme

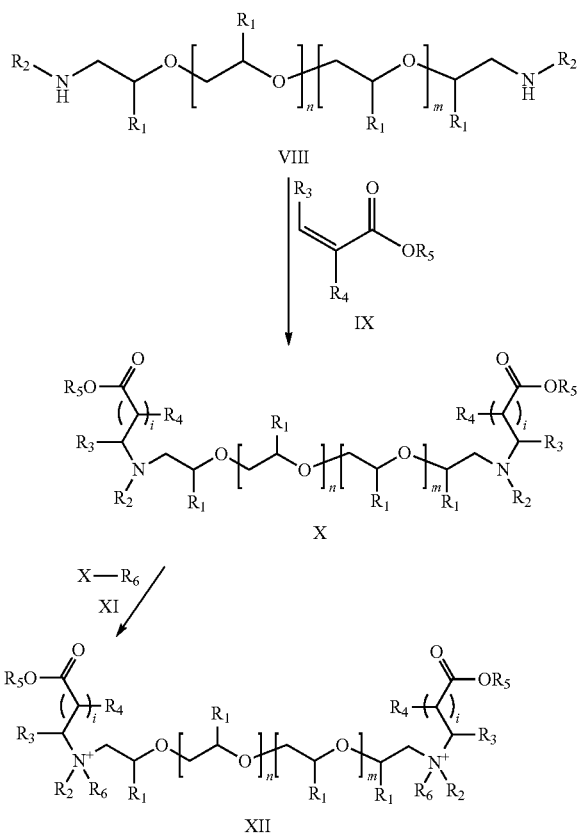

wherein the secondary amine of Formula VIII is reacted with a compound of Formula IX to obtain the compound of Formula IX to obtain the compound of Formula X, wherein said compound of Formula IX is selected from the group consisting of unsaturated alpha or beta acids and salts thereof, halogenated acids and salts thereof, and unsaturated esters, and reacting the resulting compound of Formula X with a compound of Formula XI, where X is selected from the group consisting of bromide, chloride and iodide, and $R_6$ is as defined above to obtain the compound of Formula XII.

2. The process of claim 1, wherein the ratio of the compound of Formula VIII to the compound of Formula IX is 1:1.5 to 1:4.

3. The process of claim 2, wherein the reaction of the compound of Formula VIII and the compound of Formula IX is carried out in the presence of a solvent selected from the group consisting of water, alcohol, and aromatic hydrocarbons at a temperature of 40 to 180° C. and atmospheric pressure.

4. The process of claim 3, wherein said reaction of the compound of Formula X and said compound of Formula XI is carried out at a ratio of 1:1 to 1:4.

5. The process of claim 4, wherein said reaction of the compound of Formula X and said compound of Formula XI is carried out at a temperature of 15° C. to 90° C. at a pressure of 585 to 760 mmHg.

6. The process of claim 1, wherein the compound of Formula IX is selected from the group consisting of acrylic acid, methacrylic acid, itaconic acid, crotonic acid, fumaric acid, isocrotonic acid, angelic acid, maleic acid, methyl acrylate and methyl methacrylate.

7. The process of claim 1, wherein the molar ratio of compounds of Formula VIII and IX is 1:1.8 to 1:2.6.

8. The process of claim 1, wherein the compound of Formula XI is a linear or branched alkyl or alkenyl halide and contains 1 to 30 carbon atoms.

9. The process of claim 1, wherein the compound of Formula XI is a cycloalkyl or aryl containing 5 to 12 carbon atoms.

10. The process of claim 1, wherein the molar ratio of compounds of Formula X and XI is 1:1.5 to 1:2.6.

11. The process of claim 1, wherein said compound of Formula VIII is obtained by reacting a compound of Formula I with a compound of Formula II to obtain a compound of Formula III, and thereafter reducing the compound of Formula III to obtain the secondary amine of Formula VIII, according to the following reaction scheme

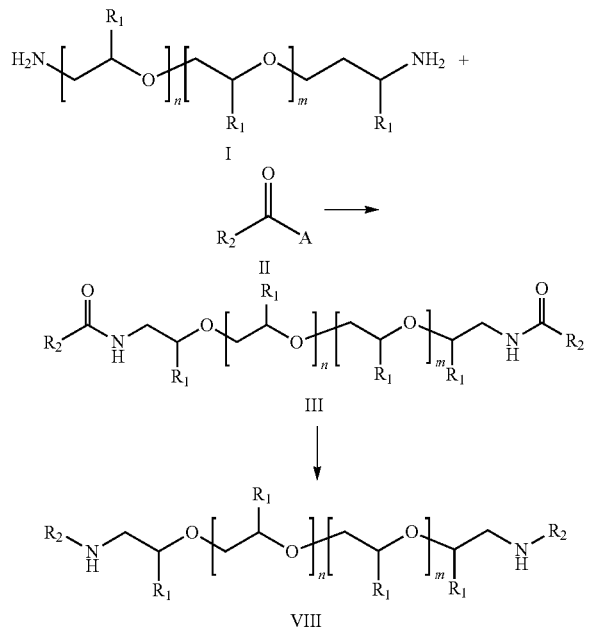

where A is selected from the group consisting of carboxylic acid, carboxylic acid ester, alkyl halide, alkenyl halide, cycloalkyl and aryl.

12. The process of claim 11, wherein said compound of Formula III is reduced to the compound of Formula VIII by reacting with a hydride or by catalytic hydrogenation.

13. The process of claim 11, wherein the compound of Formula I is a polyether derived from ethylene oxide or propylene oxide or copolymers thereof with two amino groups, one at a terminal end and the other at a beginning of the polymer chain and having a molecular weight in the range of 100 to 20,000 g/mol.

14. The process of claim 11, wherein A of the compound of Formula II is a linear or branched alkyl or alkenyl halide and contains 1 to 30 carbon atoms.

15. The process of claim 1, wherein said compound of Formula VIII is obtained by reacting a compound of Formula IV with a compound B of Formula V selected from the group consisting of tosyl chloride, mesyl chloride, bromine, chlorine, and penta or tri chloride or bromide phosphorous, to obtain the compound of Formula VI, and reacting the compound of Formula VI by nucleophilic substitution with a compound of Formula VII to obtain the compound of Formula VIII, according to the reaction scheme

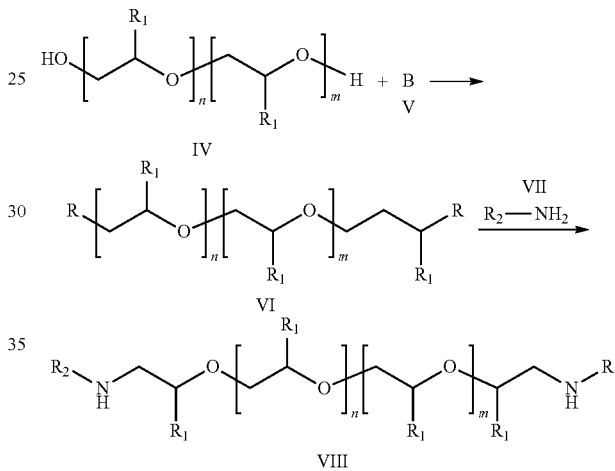

where the compound of Formula VII is selected from the group consisting of alkyl, alkenyl, cycloalkyl and aryl amines.

16. The process of claim 15, wherein said compound of Formula IV and compound B of Formula V are reacted in a ratio of 1:2 to 1:4 with sodium, potassium or cesium hydroxide at a temperature of 0-25° C.

17. The process of claim 16, wherein said compound of Formula IV and compound B of Formula V is in a solvent selected from the group consisting of water, tetrahydrofuran, acetonitrile, and mixtures thereof.

18. The process of claim 17, wherein said compound of Formula VI is reacted with said compound of Formula VII at a ratio of 1:15 to 1:4 at a temperature of 60-100° C.

19. The process of claim 18, wherein said compound of Formula VI is reacted with said compound of Formula VII in a solvent selected from the group consisting of acetonitrile, dimethylformamide, dimethylsulfoxide, acetone and short chain alcohols.

20. The process of claim 15, wherein the compound of Formula IV is a glycol derived from ethylene oxide or propylene oxide or copolymers thereof with two hydroxyl groups, one at a terminal end and the other at a beginning of the polymer chain, and has a molecular weight in the range of 100 to 20,000 g/mol.

21. The process of claim 15, wherein the molar ratio of the compound of Formula IV and compound B of Formula V is 1:2.2 to 1:2.6.

22. The process of claim 15, wherein the compound of Formula VII is linear or branched cycloalkyl or aryl amine and containing 5 to 12 carbon atoms.

23. The process of claim 15, wherein the molar ratio of compounds of Formula VI and VII is 1:1.8 to 1:2.6.

24. A method of inhibiting corrosion of ferrous metals in contact with a liquid selected from the group consisting of crude oil, liquid fuels and water, said method comprising adding a corrosion inhibitor to said liquid, said corrosion inhibitor comprising a Gemini surfactant bis-N-alkyl polyether, bis-N-alkenyl polyether, bis-N-cycloalkyl polyether, bis-N-aryl polyether bis-beta or alpha-amino acids or their salts in an amount to inhibit corrosion of said ferrous metals, wherein said Gemini surfactants have the formula

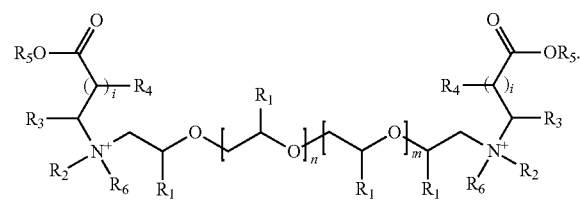

where:
$R_1$ is independently a radical represented by —H or —$CH_3$, $R_2$ is an alkyl, alkenyl chain, cycloalkyl or aryl;

$R_3$ is a radical represented by —H, —$CH_3$, —CH=CH—$CH_3$, or —COOX;

$R_4$ is a radical represented by —H, —$CH_3$, or —$CH_2$—COOX;

$R_5$ is a radical represented by —H, an alkyl, alkenyl, cycloalkyl, aryl group, or a metal;

$R_6$ is a radical represented by an alkyl, alkenyl, cycloalkyl, or aryl group;

n and m can have values from 1 to 250, and i can have values of 0 and 1:
when i=1:
$R_3$ is a radical represented by —H, —$CH_3$, —CH=CH—$CH_3$, or —COOX, and
when i is equal to 0:
$R_3$ is a radical represented by —COOX;

In the radical —COOX used in $R_3$ and $R_4$, X is represented by:

—H, an alkyl, alkenyl group, a cycloalkyl or aryl group, or a metal.

25. The method of claim 24, wherein said corrosion inhibitor comprises 1 to 100 weight percent of said Gemini surfactant.

26. The method of claim 24, wherein said corrosion inhibitor includes a solvent selected from the group consisting of distilled water, brine with a divalent ion selected from the group consisting of calcium, magnesium, strontium and barium, and organic compounds selected from the group consisting of methanol, ethanol, isopropanol, xylene, toluene, diesel, gasoline or mixtures at a concentration of 1 to 99 wt %.

27. The method of claim 24, wherein said corrosion inhibitor is present in an amount of 0.5 to 10,000 ppm.

* * * * *